Sept. 26, 1933. H. YOUNT ET AL Plant Pat. 74
APRICOT
Filed March 7, 1933
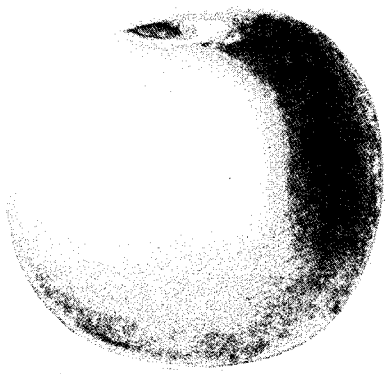
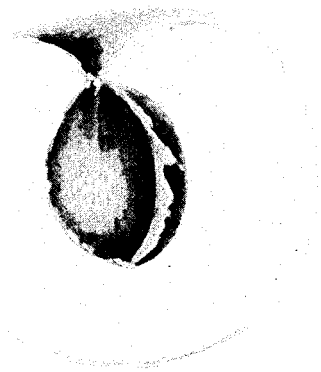
INVENTORS
Harry Yount
Andrew T. Gossman
By Orville M. Kile
PLANT PATENT AGENT Patented Sept. 26, 1933

Plant Pat. 74

UNITED STATES PATENT OFFICE

74

APRICOT

Harry Yount, Douglas County, and Andrew T. Gossman, Wenatchee, Wash.; said Yount assignor to said Gossman Application March 7, 1933. Serial No. 659,958

1 Claim. (Cl. 47—61)

Our invention relates to improvements in apricots grown for commercial purposes. This new variety is of very attractive appearance, has an excellent flavor and ripens earlier than other desirable commercial varieties.

Our new variety developed from a seed planted by the first named joint inventor who first discovered its superior qualities when this seedling came into bearing. In the year 1929 this new variety was brought to the attention of the second named joint inventor who reproduced it asexually, both by budding young stock and by top working bearing trees. Both these methods produced fruit identical with that on the original tree, thus proving the reproductive qualities of this new variety and establishing a stock of trees.

The accompanying illustrations (in the originals) show this new apricot in approximately natural size and typical color. It must be understood, however, that there will be variations in color depending upon the amount of direct exposure of the fruit to the sun, and other factors.

The trees while young are somewhat more vigorous of growth than other commercial varieties and have a more upright form.

The leaves are larger than those of the Tilton, Moorpark, Royal and Blenheim varieties, being nearly round in shape, evenly notched with small notches, and deep green in color.

The fruit is globular in shape and of large size. The axial diameter is slightly less than two inches in representative specimens and the transverse diameter at the widest point is two inches or slightly more. When grown under similar conditions our new variety is larger than the Blenheim, Tilton, or Moorpark but smaller than the Wenatchee.

The cavity is regular in form and medium deep.

The suture is medium to shallow in depth.

The stone is somewhat smaller than that of the Moorpark and entirely free from the flesh when ripe. The dorsal suture of the stone has rather prominent protuberances or "fins."

The skin is exceptionally smooth, thereby heightening the striking color effect.

The color is an attractive yellowish-orange shading to deep dark red where the fruit is exposed to the sunlight. Portions of the surface may be any shade between pale yellow and deep red, thus tan and orange shades are present on nearly every fruit.

The flesh is firm in texture and of a desirable "apricot-yellow" color. The flavor may be described as excellent and distinctive.

This apricot ripens seven to ten days earlier than the Wenatchee variety (the earliest commercial variety grown in the Wenatchee region) and at least three weeks earlier than the Tilton. The blooming date is, however, approximately the same as for the Wenatchee.

The combination of principal features which make this new apricot a superior commercial variety are:

1. Its extreme earliness of ripening.
2. Its smooth skin and very attractive coloring.
3. Its excellent flavor and shipping qualities.
4. The vigorous growth of the young trees.

Having thus disclosed our invention, we claim:

The variety of apricot herein shown and described, characterized particularly by the early ripening of its fruit which is unusually attractive in coloration and has an excellent flavor as well as other desirable commercial qualities.

HARRY YOUNT.
A. T. GOSSMAN.